(12) United States Patent
Ewald et al.

(10) Patent No.: US 11,406,351 B2
(45) Date of Patent: Aug. 9, 2022

(54) ULTRASOUND IMAGING METHOD (71) Applicant: KONINKLIJKE PHILIPS N.V., Eindhoven (NL)

(72) Inventors: Arne Ewald, Hamburg (DE); Irina Waechter-Stehle, Hamburg (DE); Frank Michael Weber, Hamburg (DE); Tobias Wissel, Lübeck (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 297 days.

(21) Appl. No.: 16/619,216

(22) PCT Filed: May 30, 2018

(86) PCT No.: PCT/EP2018/064123
§ 371 (c)(1),
(2) Date: Dec. 4, 2019

(87) PCT Pub. No.: WO2018/224363
PCT Pub. Date: Dec. 13, 2018

(65) Prior Publication Data
US 2020/0163645 A1 May 28, 2020

(30) Foreign Application Priority Data

Jun. 8, 2017 (EP) .................................... 17174951

(51) Int. Cl.
*G06K 9/00* (2022.01)
*A61B 8/14* (2006.01)
(Continued)

(52) U.S. Cl.
CPC ............ *A61B 8/0883* (2013.01); *A61B 8/463* (2013.01); *A61B 8/481* (2013.01); *A61B 8/5246* (2013.01);
(Continued)

(58) Field of Classification Search
USPC ....... 382/100, 103, 107, 128–134, 154, 162, 382/173, 181, 219, 224, 254, 274,
(Continued)

(56) References Cited

U.S. PATENT DOCUMENTS

2008/0095415 A1* 4/2008 Hall ..................... A61B 8/0883
382/128
2009/0187106 A1* 7/2009 Lee ..................... G01S 15/8963
600/458
(Continued)

FOREIGN PATENT DOCUMENTS

| EP | 2082688 A1 | 7/2009 |
|---|---|---|
| WO | 2010020933 A2 | 2/2010 |
| WO | 2015189160 A1 | 12/2015 |

OTHER PUBLICATIONS

Jenkins, et al., "Left ventricular volume measurement with echocardiography: a comparison of left ventricular opacification, three-dimensional echocardiography, or both with magnetic resonance imaging", European Heart Journal (2009), 30, pp. 98-106.
(Continued)

*Primary Examiner* — Seyed H Azarian (57) ABSTRACT

Provided is a method (200) for generating a combined anatomical model of a heart. The method comprises receiving (220) a non-contrast agent-enhanced ultrasound image of a left ventricular region of the heart and receiving (240) a contrast agent-enhanced ultrasound image of the left ventricular region of the heart. Image registration (260) is performed on the respective non-contrast agent-enhanced and contrast agent-enhanced ultrasound images, such that the respective images are aligned. Combined segmentation (270) of the aligned non-contrast agent-enhanced and contrast agent-enhanced ultrasound images is then carried out to generate the combined anatomical model. The combined segmentation (270) uses features of both of the aligned
(Continued)

non-contrast agent-enhanced and contrast agent-enhanced ultrasound images as target points. Further provided is a processor arrangement adapted to implement the method and an ultrasound system comprising the processor arrangement. A computer program product comprising computer program code means adapted to implement the method is also provided.

20 Claims, 3 Drawing Sheets

(51) Int. Cl.
*A61B 8/08* (2006.01)
*G06T 7/10* (2017.01)
*G06T 7/30* (2017.01)
*A61B 8/00* (2006.01)
*G06T 7/00* (2017.01)

(52) U.S. Cl.
CPC .............. *G06T 7/0012* (2013.01); *G06T 7/10* (2017.01); *G06T 7/30* (2017.01); *G06T 2207/10132* (2013.01); *G06T 2207/20212* (2013.01); *G06T 2207/30048* (2013.01)

(58) Field of Classification Search
USPC .................. 382/285–291, 305, 319; 600/458
See application file for complete search history.

(56) References Cited

U.S. PATENT DOCUMENTS

| | | |
|---|---|---|
| 2013/0035596 A1 | 2/2013 | Ionasec et al. |
| 2013/0294667 A1* | 11/2013 | Zheng ...................... G06T 7/00 382/131 |
| 2014/0219524 A1 | 8/2014 | Takeguchi et al. |
| 2015/0213613 A1* | 7/2015 | Prevost ................. G06T 3/0006 382/131 |
| 2016/0180521 A1* | 6/2016 | Mountney ............ A61B 6/5235 382/131 |

OTHER PUBLICATIONS

International Search Report and Written Opinion for International Application No. PCT/EP2018/064123, dated May 30, 2018, 14 pages.
Ecabert, et al., "Automatic Model-Based Segmentation of the Heart in CT Images", Medical Imaging, IEEE Transactions on, Sep. 2008, vol. 27, pp. 1189-1201. (Abstract).
Chahal, et al., "Clinical Applications of Left Ventricular Opacification", JACC: Cardiovascular Imaging, vol. 3, No. 2, Feb. 2010, pp. 188-196.

* cited by examiner

FIG. 3

ULTRASOUND IMAGING METHOD

RELATED APPLICATIONS

This application is the U.S. National Phase application under 35 U.S.C. § 371 of International Application No. PCT/EP2018/064123, filed on May 30, 2018, which claims the benefit of European Application No. 17174951.8, filed Jun. 8, 2017. These applications are hereby incorporated by reference herein.

FIELD OF THE INVENTION

This invention relates to image processing of contrast agent-enhanced and non-contrast agent-enhanced ultrasound images of the heart.

BACKGROUND OF THE INVENTION

Ultrasound imaging is increasingly being employed in a variety of different applications. It is important that the image produced by the ultrasound system is as clear and accurate as possible so as to give the user a realistic interpretation of the subject being scanned. This is especially the case when the subject in question is a patient undergoing a medical ultrasound scan. In this situation, the ability of a physician to make an accurate diagnosis is dependent on the quality of the image produced by the ultrasound system.

Due to its excellent temporal resolution and its non-invasiveness, ultrasound plays an important role in cardio-vascular imaging. Most commonly, Transthoracic Echo (TTE) imaging is used to determine left ventricular quantities such as volume or ejection fraction. To minimize manual effort and user variability, this process has been automated by employing anatomically intelligent model-based segmentation (Ecabert, O. et al.; IEEE Transactions on, 2008, 27, pp. 1189-1201).

However, TTE imaging has disadvantages relating to image quality which can hamper determination of left ventricular quantities. In particular, TTE imaging has limitations in terms of endocardial border resolution and can be prone to underestimation of both volume and ejection fraction.

These issues have necessitated the development of another ultrasound technique called left ventricle opacification (LVO). In LVO, a contrast agent is used to provide greater contrast between the blood in the left ventricular cavity and the myocardium. The contrast agent may be administered intravenously in order to reach the heart. Contrast agents tend to take the form of gas microbubbles encapsulated by a suitable polymer shell. The gas microbubbles provide enhanced backscatter of ultrasound waves relative to the surrounding tissue thereby enhancing the contrast between the blood in the left ventricular cavity and the myocardium.

In practice, an initial scan is typically performed without employing a contrast agent, i.e. using TTE imaging. In the event that the physicians are not satisfied with the image quality of the initial scan which may be more likely in the case of, for example, obese patients, an additional scan using a contrast agent is performed, i.e. using LVO imaging.

However, LVO imaging is not without disadvantages. In particular, important structures such as the mitral valve are not observable in LVO images; the left ventricular cavity dominating the image. This prevents segmentation of such structures using LVO images.

Moreover, the absence of structures such as the mitral valve in the LVO image can also hamper determination of left ventricular quantities. For example, the error in measuring the left ventricular volume will be much higher if the mitral valve plane is not or not properly visible in the image, because the basal limit of the volume is not properly defined.

The distribution of the contrast agent may also be inhomogeneous which renders segmentation of LVO images, e.g. using model-based segmentation, more difficult.

A further problem relates to the scenario in which the TTE and LVO images are segmented sequentially, i.e. in order to obtain all the available information. In such a scenario, the physician may wish to merge the two separate segmentations and therefore must decide which one is more trustable in a given region of the image. In other words, the onus is placed on the physician to combine different and possibly inconsistent image information. Furthermore, this task may be made more difficult if the TTE and LVO images are not sufficiently closely aligned.

In published patent application US 2013/035596 A1, it is there disclosed a model-based positioning method for intracardiac echocardiography volume stitching, in which different volumes of a patient are scanned, then spatially aligned and finally stitched together, creating a larger volume. The alignment is based on feature and/or surface matching of the intracardiac echocardiography volumes with a preoperative model of the same patient, and the matching with the model indicates a relative position of the volumes with each other.

SUMMARY OF THE INVENTION

The present invention seeks to provide a method of cardiac segmenting which combines the respective advantages of contrast agent-enhanced and non-contrast agent-enhanced ultrasound imaging.

The invention is defined by the claims.

In accordance with an aspect, there is provided a method for generating a combined anatomical model of a heart, the method comprising: receiving a non-contrast agent-enhanced ultrasound image of a left ventricular region of the heart; receiving a contrast agent-enhanced ultrasound image of the left ventricular region of the heart; aligning the non-contrast agent-enhanced and contrast agent-enhanced ultrasound images; and performing a combined segmentation of the aligned non-contrast agent-enhanced and contrast agent-enhanced ultrasound images to generate the combined anatomical model, wherein performing the combined segmentation comprises using features of both of the aligned non-contrast agent-enhanced and contrast agent-enhanced ultrasound images as target points.

The present invention is based on the realization that by performing a combined segmentation using the aligned, i.e. registered, non-contrast agent-enhanced and contrast agent-enhanced images, a more accurate and robust segmentation can be obtained compared to that which can be obtained from, for instance, the non-contrast agent-enhanced ultrasound image alone. This is due to the combined segmentation using the information available from the contrast agent-enhanced ultrasound image. Moreover, the combined segmentation also makes use of the information available from the non-contrast agent-enhanced ultrasound image, i.e. relating to other cardiac structures such as the mitral valve, which are not visible in the contrast agent-enhanced ultrasound image. In this way, the generation of the combined anatomical model exploits the information available from both the non-contrast agent-enhanced and contrast agent-enhanced ultrasound imaging techniques.

Owing to the differences in the nature and quality of the information available from the respective contrast agent-enhanced and non-contrast agent-enhanced ultrasound images, target points corresponding to the contrast agent-enhanced and non-contrast agent-enhanced components of the aligned image are both used in the combined segmentation. This assists in exploiting the complementary information available from the respective non-contrast agent-enhanced and contrast agent-enhanced ultrasound imaging techniques.

The combined segmentation may, for instance, be a model-based segmentation. The combined segmentation may thus comprise adapting a generic anatomical model, e.g. an initial mesh model corresponding to a mean shape of the organ derived from multiple training images, to the aligned non-contrast agent-enhanced and contrast agent-enhanced ultrasound images, in order to attain the combined anatomical model. If a model-based segmentation is employed which makes use of a mesh model, the combined anatomical model may be alternatively termed as a combined mesh model. Other model-based segmentation models are conceivable which may employ alternative means, i.e. other than a 'mesh', to represent the surface of the anatomical feature.

In an embodiment, the method may further comprise: performing a first segmentation of the non-contrast agent-enhanced ultrasound image to generate a first anatomical model; and performing a second segmentation of the contrast agent-enhanced ultrasound image to generate a second anatomical model, wherein the aligning the non-contrast agent-enhanced and contrast agent-enhanced ultrasound images comprises registration of the first and second anatomical models.

Use of the first and second anatomical models for alignment of the contrast agent-enhanced and non-contrast agent-enhanced ultrasound images may facilitate and improve the quality, i.e. closeness, of the alignment.

The performing a second segmentation may comprise using the first anatomical model to initialize the second segmentation. Thus the first anatomical model may be used instead of, for instance, a mean shape obtained from a plurality of training images, in the initializing of the second segmentation. This may enhance the efficiency and quality of the second segmentation because the first anatomical model may be closer than the mean shape to the actual organ shape of the patient.

The receiving a contrast agent-enhanced ultrasound image may comprise combining a plurality of ultrasound image frames obtained during respective heart cycles in which a contrast agent is present. Obtaining this plurality of ultrasound image frames may be carried out with a near-constant probe position such that the plurality of images may be closely aligned with respect to each other. However, the distribution of the contrast agent in each of the plurality of images may be different. Combining the plurality of image frames may assist to correct for this non-uniform contrast agent distribution.

When the combined segmentation is a model-based segmentation, target points from both of the respective contrast agent-enhanced and non-contrast agent-enhanced ultrasound images may be used in the process of adapting a generic anatomical model, e.g. an initial mesh model, to the aligned non-contrast agent-enhanced and contrast agent-enhanced ultrasound images, in order to attain the combined anatomical model.

The aligning of the non-contrast agent-enhanced and contrast agent-enhanced ultrasound images and the performing the combined segmentation may be repeated in a plurality of cycles. The quality of the combined segmentation may at least partly depend on the quality, i.e. closeness, of the alignment of the images. The alignment of the images may also be enhanced by a better segmentation, particularly when the alignment is performed via prior segmentation steps, i.e. the first and second segmentation steps. Hence repeating, i.e. iterating, this procedure may improve the combined segmentation result.

In accordance with another aspect, there is provided a computer program comprising computer program code means which is adapted, when the computer program is run on a computer, to implement the method described above.

In accordance with still another aspect, there is provided a processor arrangement for controlling the generation of a combined anatomical model of a heart, wherein the processor arrangement is adapted to: receive a non-contrast agent-enhanced ultrasound image of a left ventricular region of the heart; receive a contrast agent-enhanced ultrasound image of the left ventricular region of the heart; align the non-contrast agent-enhanced and contrast agent-enhanced ultrasound images; and perform a combined segmentation of the aligned non-contrast agent-enhanced and contrast agent-enhanced ultrasound images to generate the combined anatomical model.

In accordance with a further aspect, there is provided an ultrasound system comprising: an ultrasonic transducer array, wherein the ultrasonic transducer array is capable of emitting and receiving ultrasonic signals; a signal processor adapted to compile the received ultrasonic signals into a non-contrast agent-enhanced ultrasound image when no contrast agent is used, and a contrast agent-enhanced ultrasound image when a contrast agent is used; a processor arrangement as described above; a conversion module adapted to convert the combined anatomical model generated by the processor arrangement to a combined segmented image; a display device for displaying the combined segmented ultrasound image; and a user interface adapted to permit a user to control the processor arrangement to generate the combined anatomical model.

The user interface may also be adapted to permit user selection of the viewing plane of the displayed combined segmented ultrasound image. Owing to the alignment of the contrast agent-enhanced and non-contrast agent-enhanced ultrasound images for generation of the combined anatomical model and thus the combined segmented image, the respective images are thus anatomically synchronized. Accordingly, when the viewing plane is adjusted for the non-contrast agent-enhanced image, the contrast agent-enhanced image will be also adjusted to the same viewing plane, and vice versa. This is of clear benefit in terms of facilitating visual comparison of the respective images.

The processor arrangement may be adapted to implement a post-visualization routine comprising a further aligning of the non-contrast agent-enhanced and contrast agent-enhanced ultrasound images and a further performing of the combined segmentation, the user interface being adapted to permit the user to trigger the post-visualization routine. The user may thus opt to seek improvement of the combined anatomical model by triggering the processor arrangement to implement the further alignment and further combined segmentation steps.

The processor arrangement may be adapted to invert the contrast agent-enhanced ultrasound image, to normalize the inverted contrast agent-enhanced ultrasound image based on the non-contrast agent-enhanced ultrasound image, and to control the display device to display the inverted and normalized contrast agent-enhanced ultrasound image. The contrast agent-enhanced image may show the left ventricle as a brighter region in comparison to, for instance, the myocardium. On the other hand, in the non-contrast agent-enhanced image the myocardium may show up brighter than the left ventricle but the contrast between the two regions may be lower than in the contrast agent-enhanced image. Thus inverting the contrast agent-enhanced ultrasound image and normalizing it based on the non-contrast agent-enhanced ultrasound image may facilitate visual comparison of the respective images.

The processor arrangement may be adapted to overlay the non-contrast agent-enhanced ultrasound image, the contrast agent-enhanced ultrasound image and the combined segmented image, and to control the display device to display the overlay. The user interface may be adapted to permit user adjustment of the relative contributions of the non-contrast agent-enhanced and contrast agent-enhanced ultrasound images in the overlay. The user interface may comprise a dial or slider for this user adjustment.

The processor arrangement may be adapted to control the display device such that the combined segmented ultrasound image is displayed in separate image panes which respectively comprise the non-contrast agent-enhanced and contrast agent-enhanced ultrasound images. The processor arrangement may be adapted to modify the combined segmented image displayed in both image panes in response to user instructions to modify the combined anatomical model, wherein the user interface comprises controls for inputting the user instruction. The user may thus straightforwardly assess any modification to the combined anatomical model with reference to both the contrast agent-enhanced and non-contrast agent-enhanced images.

BRIEF DESCRIPTION OF THE DRAWINGS

Embodiments of the invention are described in more detail and by way of non-limiting examples with reference to the accompanying drawings, wherein.

DETAILED DESCRIPTION OF THE EMBODIMENTS

The invention will be described with reference to the Figures. It should be understood that the detailed description and specific examples, while indicating exemplary embodiments of the apparatus, systems and methods, are intended for purposes of illustration only and are not intended to limit the scope of the invention. These and other features, aspects, and advantages of the apparatus, systems and methods of the present invention will become better understood from the following description, appended claims, and accompanying drawings. It should be understood that the Figures are merely schematic and are not drawn to scale. It should also be understood that the same reference numerals are used throughout the Figures to indicate the same or similar parts.

Provided is a method for generating a combined anatomical model of a heart. The method comprises receiving a non-contrast agent-enhanced ultrasound image of a left ventricular region of the heart and receiving a contrast agent-enhanced ultrasound image of the left ventricular region of the heart. Image registration is performed on the respective non-contrast agent-enhanced and contrast agent-enhanced ultrasound images, such that the respective images are aligned. A combined segmentation of the aligned non-contrast agent-enhanced and contrast agent-enhanced ultrasound images is then carried out to generate the combined anatomical model. The combined segmentation uses features of both of the aligned non-contrast agent-enhanced and contrast agent-enhanced ultrasound images as target points.

Figure 1:
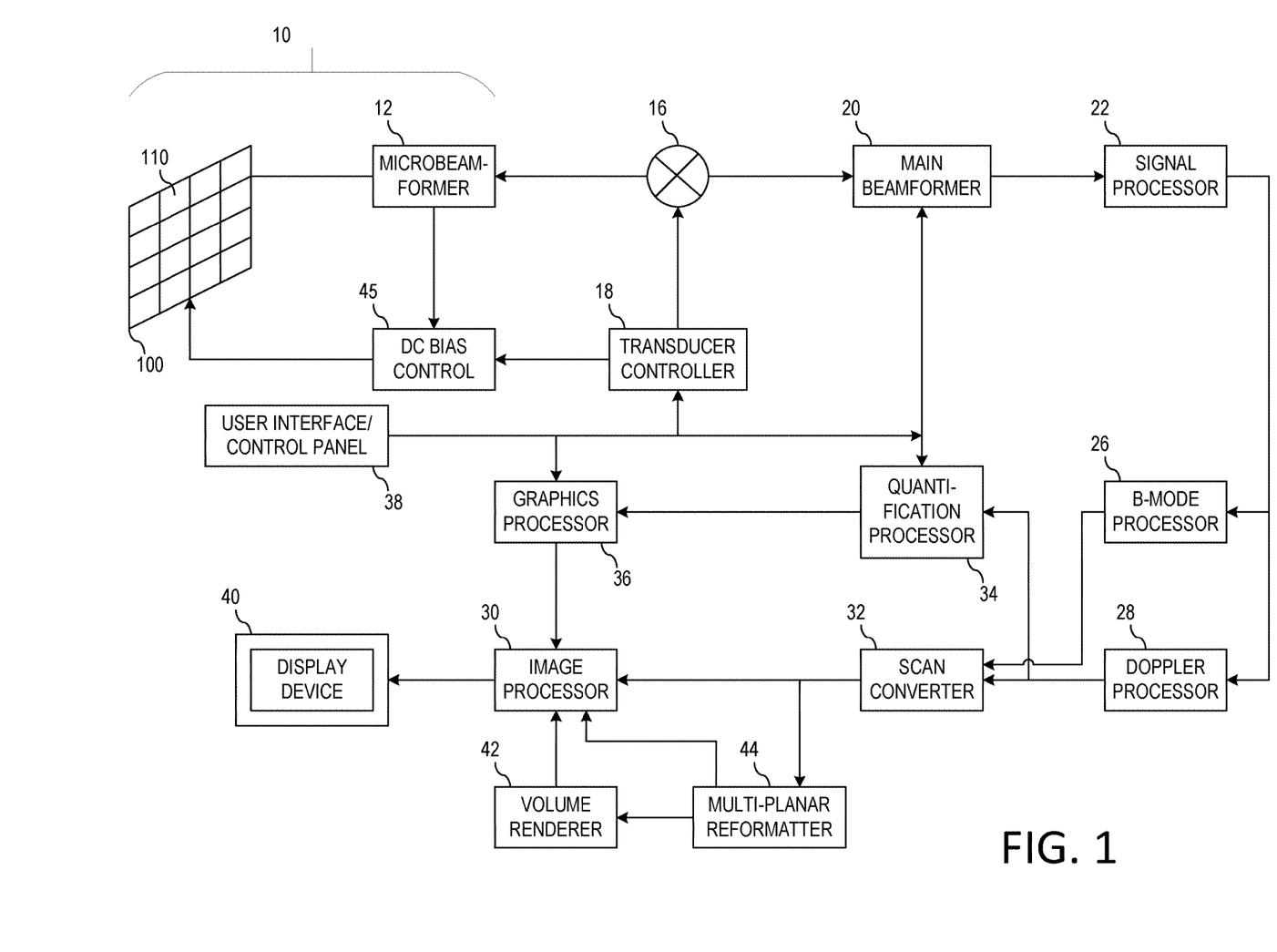
FIG. 1 shows an ultrasound diagnostic imaging system to explain the general operation.

The general operation of an exemplary ultrasound diagnostic imaging system will first be described, with reference to FIG. 1.

The system comprises an array transducer probe 10 which has a CMUT transducer array 100 for transmitting ultrasound waves and receiving echo information. The transducer array 100 may alternatively comprise piezoelectric transducers formed of materials such as PZT or PVDF. The transducer array 100 is a two-dimensional array of transducers 110 capable of scanning in a 2D plane or in three dimensions for 3D imaging. In another example, the transducer array 100 may be a 1D array.

The transducer array 100 is coupled to a microbeamformer 12 in the probe which controls reception of signals by the CMUT array cells or piezoelectric elements. Microbeamformers are capable of at least partial beamforming of the signals received by sub-arrays (or "groups" or "patches") of transducers as described in U.S. Pat. No. 5,997,479 (Savord et al.), U.S. Pat. No. 6,013,032 (Savord), and U.S. Pat. No. 6,623,432 (Powers et al.).

Note that the microbeamformer is entirely optional. The examples below assume no analog beamforming.

The microbeamformer 12 is coupled by the probe cable to a transmit/receive (T/R) switch 16 which switches between transmission and reception and protects the main beamformer 20 from high energy transmit signals when a microbeamformer is not used and the transducer array 100 is operated directly by the main system beamformer. The transmission of ultrasound beams from the transducer array 100 is directed by a transducer controller 18 coupled to the microbeamformer by the T/R switch 16 and a main transmission beamformer (not shown), which receives input from the user's operation of the user interface or control panel 38.

One of the functions controlled by the transducer controller 18 is the direction in which beams are steered and focused. Beams may be steered straight ahead from (orthogonal to) the transducer array 100, or at different angles for a wider field of view. The transducer controller 18 can be coupled to control a DC bias control 45 for the CMUT array. The DC bias control 45 sets DC bias voltage(s) that are applied to the CMUT cells.

In the reception channel, partially beamformed signals are produced by the microbeamformer 12 and are coupled to a main receive beamformer 20 where the partially beamformed signals from individual patches of transducers are combined into a fully beamformed signal. For example, the main beamformer 20 may have 128 channels, each of which receives a partially beamformed signal from a patch of dozens or hundreds of CMUT transducer cells or piezoelectric elements. In this way the signals received by thousands of transducers of a transducer array 100 can contribute efficiently to a single beamformed signal.

The beamformed reception signals are coupled to a signal processor 22. The signal processor 22 can process the received echo signals in various ways, such as band-pass filtering, decimation, I and Q component separation, and harmonic signal separation which acts to separate linear and nonlinear signals so as to enable the identification of nonlinear (higher harmonics of the fundamental frequency) echo signals returned from tissue and microbubbles. The signal processor may also perform additional signal enhancement such as speckle reduction, signal compounding, and noise elimination. The band-pass filter in the signal processor can be a tracking filter, with its pass band sliding from a higher frequency band to a lower frequency band as echo signals are received from increasing depths, thereby rejecting the noise at higher frequencies from greater depths where these frequencies are devoid of anatomical information.

The beamformers for transmission and for reception are implemented in different hardware and can have different functions. Of course, the receiver beamformer is designed to take into account the characteristics of the transmission beamformer. In FIG. 1 only the receiver beamformers 12, 20 are shown, for simplicity. In the complete system, there will also be a transmission chain with a transmission micro beamformer, and a main transmission beamformer.

The function of the micro beamformer 12 is to provide an initial combination of signals in order to decrease the number of analog signal paths. This is typically performed in the analog domain.

The final beamforming is done in the main beamformer 20 and is typically after digitization.

The transmission and reception channels use the same transducer array 100 which has a fixed frequency band. However, the bandwidth that the transmission pulses occupy can vary depending on the transmission beamforming that has been used. The reception channel can capture the whole transducer bandwidth (which is the classic approach) or by using bandpass processing it can extract only the bandwidth that contains the useful information (e.g. the harmonics of the main harmonic).

The processed signals are coupled to a B mode (i.e. brightness mode, or 2D imaging mode) processor 26 and a Doppler processor 28. The B mode processor 26 employs detection of an amplitude of the received ultrasound signal for the imaging of structures in the body such as the tissue of organs and vessels in the body. B mode images of structure of the body may be formed in either the harmonic image mode or the fundamental image mode or a combination of both as described in U.S. Pat. No. 6,283,919 (Roundhill et al.) and U.S. Pat. No. 6,458,083 (Jago et al.) The Doppler processor 28 processes temporally distinct signals from tissue movement and blood flow for the detection of the motion of substances such as the flow of blood cells in the image field. The Doppler processor 28 typically includes a wall filter with parameters which may be set to pass and/or reject echoes returned from selected types of materials in the body.

The structural and motion signals produced by the B mode and Doppler processors are coupled to a scan converter 32 and a multi-planar reformatter 44. The scan converter 32 arranges the echo signals in the spatial relationship from which they were received in a desired image format. For instance, the scan converter may arrange the echo signal into a two dimensional (2D) sector-shaped format, or a pyramidal three dimensional (3D) image. The scan converter can overlay a B mode structural image with colors corresponding to motion at points in the image field with their Doppler-estimated velocities to produce a color Doppler image which depicts the motion of tissue and blood flow in the image field. The multi-planar reformatter will convert echoes which are received from points in a common plane in a volumetric region of the body into an ultrasound image of that plane, as described in U.S. Pat. No. 6,443,896 (Detmer). A volume renderer 42 converts the echo signals of a 3D data set into a projected 3D image as viewed from a given reference point as described in U.S. Pat. No. 6,530,885 (Entrekin et al.).

The 2D or 3D images are coupled from the scan converter 32, multi-planar reformatter 44, and volume renderer 42 to an image processor 30 for further enhancement, buffering and temporary storage for display on a display device 40. In addition to being used for imaging, the blood flow values produced by the Doppler processor 28 and tissue structure information produced by the B mode processor 26 are coupled to a quantification processor 34. The quantification processor 34 produces measures of different flow conditions such as the volume rate of blood flow as well as structural measurements such as the sizes of organs and gestational age. The quantification processor 34 may receive input from the user control panel 38, such as the point in the anatomy of an image where a measurement is to be made. Output data from the quantification processor 34 is coupled to a graphics processor 36 for the reproduction of measurement graphics and values with the image on the display 40, and for audio output from the display device 40. The graphics processor 36 can also generate graphic overlays for display with the ultrasound images. These graphic overlays can contain standard identifying information such as patient name, date and time of the image, imaging parameters, and the like. For these purposes the graphics processor receives input from the user interface 38, such as patient name. The user interface 38 is also coupled to the transmit controller 18 to control the generation of ultrasound signals from the transducer array 100 and hence the images produced by the transducer array 100 and the ultrasound system. The transmit control function of the controller 18 is only one of the functions performed. The controller 18 also takes account of the mode of operation (given by the user) and the corresponding required transmitter configuration and band-pass configuration in the receiver analog to digital converter. The controller 18 can be a state machine with fixed states.

The user interface 38 is also coupled to the multi-planar reformatter 44 for selection and control of the planes of multiple multi-planar reformatted (MPR) images which may be used to perform quantified measures in the image field of the MPR images.

A processor arrangement may be adapted to perform any part of the method described below with reference to FIGS. 2 and 3. The processor arrangement may, for instance, be included in one or more of the previously described processors, such as the controller 18, the quantification processor 34 and the graphics processor 36. Alternatively, the processor arrangement may be an additional module.

In an embodiment, the method described below with reference to FIGS. 2 and 3 may be implemented by a computer program code, included in a computer program product, which is run on a computer.

Figure 2:
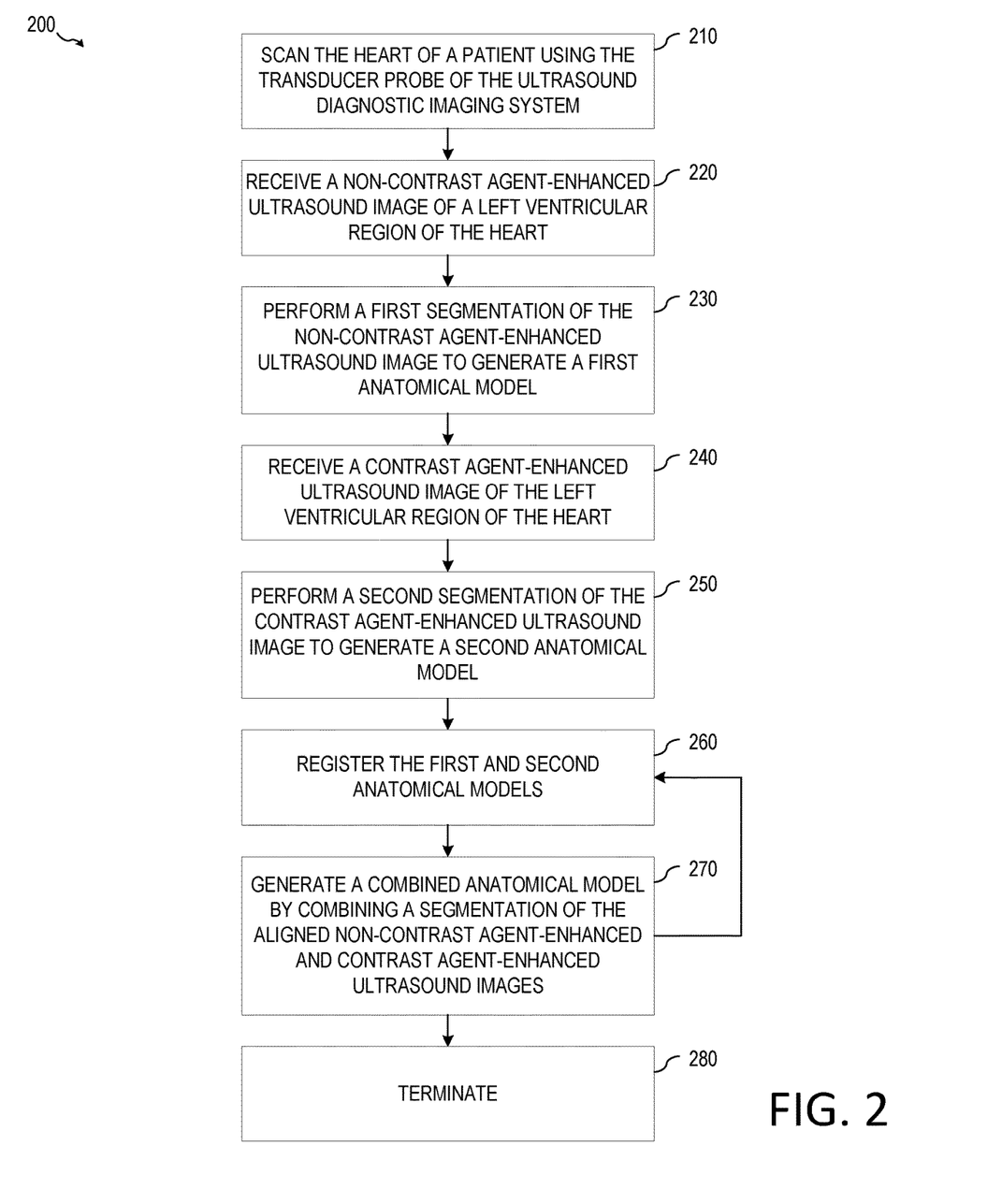
FIG. 2 shows a flowchart of a method according to an embodiment.

FIG. 2 shows a flowchart of the method 200 for controlling the generation of a segmented ultrasound image of a heart according to an embodiment. The method 200 commences in step 210. Step 210 may, for instance, correspond to scanning the heart of a patient using the transducer probe 10 of the ultrasound diagnostic imaging system described above.

In step 220, a non-contrast agent-enhanced ultrasound image of a left ventricular region of the heart is received. This non-contrast agent-enhanced ultrasound image may, for instance, be a standard transthoracic echo (TTE) image. There are four standard positions which permit visualization of different portions of the heart: the parasternal position, the apical position, the subcostal position and the suprasternal notch position. The apical position permits inter alia evaluation of left ventricular motion and evaluation of left ventricular thrombus, as well as assessment of flow across the mitral valve. Accordingly, the non-contrast agent-enhanced image ultrasound image may be obtained from the apical position in order to attain the non-contrast agent-enhanced ultrasound image of the left ventricular region. Of course, other positions, e.g. non-standard positions, may also be used. Non-contrast agent-enhanced ultrasound imaging such as TTE is well-known per se, and will not be further elaborated on herein for the sake of brevity only.

In step 240, a contrast agent-enhanced ultrasound image of the left ventricular region of the heart is received. This contrast agent-enhanced ultrasound image may be obtained using a left ventricle opacification (LVO) technique. As is well-known per se, a suitable contrast agent may be injected intravenously via a cannula. This may be administered as a slow bolus followed by a slow saline flush. Such an injection protocol may assist in providing a uniform opacification of the left ventricle. Other methods are also known such as continuous infusion of the contrast agent. The contrast agent itself may, for instance, be a microbubble-based agent in which a gas is encapsulated by a biocompatible polymer. Other types contrast agents may also be used.

It is noted at this point that it may be desirable to adopt a different mode, e.g. switching to harmonic image mode, of the ultrasound system for obtaining the contrast agent-enhanced ultrasound image. The mode may be changed prior to administering the contrast agent by, for instance, pushing a button on the user interface 38 such that the controller 18 is triggered to switch to the desired mode.

The contrast agent-enhanced image ultrasound image may be obtained from the same position as the non-contrast agent-enhanced image ultrasound image, or as close as possible, thereby to assist with the aligning 260 of the respective images. For example, the apical position may be used to obtain both the contrast agent-enhanced and non-contrast agent-enhanced ultrasound images.

In an embodiment, the step 240 of receiving a contrast agent-enhanced ultrasound image may comprise combining a plurality of ultrasound image frames obtained during respective heart cycles in which a contrast agent is present. A plurality of heart cycles may be recorded such that a plurality of ultrasound image frames corresponding to a particular point in the heart cycle, e.g. the end diastolic (ED) phase, can be collected.

Such a recording may be obtained with a constant probe position such that the images are aligned or near-aligned with respect to each other. However, the distribution of contrast agent in each of the plurality of images may be different. This non-uniform contrast agent distribution may be corrected for by combining the plurality of image frames. In other words, a bias due to an inhomogeneous distribution of contrast agent may thus be reduced. This combining may, for instance, be achieved by taking the maximum value of intensity for each individual voxel. Accordingly, this combining approach may also assist to enhance the contrast in the contrast agent-enhanced ultrasound image.

In the flowchart shown in FIG. 2, step 240 is carried out after step 220. This order partly reflects the protocol which is commonly used in practice, but is not intended to be limiting. It is also conceivable that the contrast agent-enhanced image may be received before the non-contrast agent-enhanced image, providing that sufficient dissipation of the contrast agent is permitted.

In step 260, the non-contrast agent-enhanced and contrast agent-enhanced ultrasound images are aligned. Step 260 may be alternatively termed as image registration of the non-contrast agent-enhanced and contrast agent-enhanced ultrasound images. Step 260 may be achieved using any suitable image registration algorithm. This registration step 260 may serve to compensate for any misalignment of the contrast agent-enhanced and non-contrast agent-enhanced ultrasound images stemming from probe movement between the respective acquisitions, e.g. between the TTE and LVO acquisitions.

Owing to the fact that the respective images are of the same organ, a rigid, e.g. linear, image registration technique may be used. Given that image registration techniques, particularly in the field of medical imaging, are well-known per se, such techniques will not be further described in general terms herein for the sake of brevity only.

In an embodiment, the method 200 further comprises performing 230 a first segmentation of the non-contrast agent-enhanced ultrasound image to generate a first anatomical model and performing 250 a second segmentation of the contrast agent-enhanced ultrasound image to generate a second anatomical model. In this embodiment, the aligning 260 the non-contrast agent-enhanced and contrast agent-enhanced ultrasound images comprises registration of the first and second anatomical models.

Figure 3:
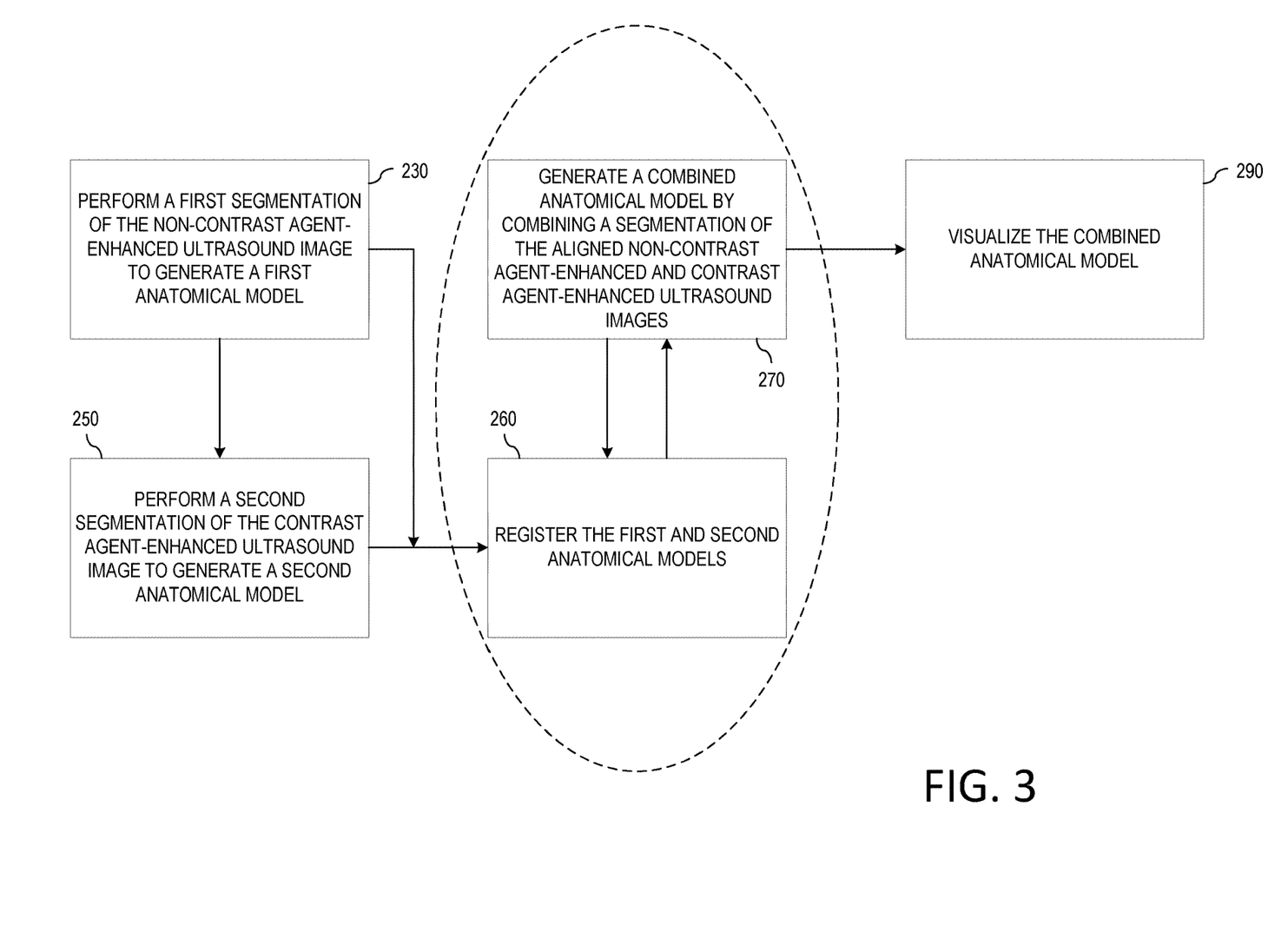
FIG. 3 shows a flowchart including some of the method steps shown in FIG. 2.

This embodiment is also depicted in the flowchart shown in FIG. 3 which shows the first segmentation 230 followed by the second segmentation 250. The resulting first and second anatomical models are then used for the image registration in step 260. Any suitable segmentation technique may be used for steps 230 and 250. In non-limiting examples, a model-based segmentation technique may be employed.

Known model-based segmentations are based on a triangle mesh model which is adapted to the boundaries of an organ in an image, i.e. the heart in this case. Other polygonal meshes are also conceivable. The initial triangle mesh model corresponds to a mean shape of the organ which derives from multiple training images. The segmentation may be achieved by minimizing a total energy function consisting of two summed terms: an internal energy function and an external energy function. The internal energy function applies shape constraint and the external energy function describes how well the model fits to the image. A known example of such a total energy function ($E_{tot}$) is provided in Equation 1.

$$E_{tot} = \sum_{i=1}^{V} \sum_{j \in N(i)} \sum_{k=1}^{K} \omega_{i,k} ((v_i - v_j) - (T_k[m_i] - T_k([m_j]))^2 + \alpha \cdot \sum_i w_i \cdot D(x_i^{target}, c_i)^2$$

Equation 1

The left hand term in Equation 1 is the internal energy function ($E_{int}$) and the right hand term in Equation 1 is the external energy function ($E_{ext}$).

For each mesh triangle i, a target point $x_i^{target}$ is searched along the normal vector of the triangle i. A reliability function $w_i$ increases with feature response and decreases with the distance between the target point and the initial triangle. The function $D(x_i^{target}, c_i)$ describes the deviation between the target point $x_i^{target}$ and the center of the triangle $c_i$. In this way, minimizing $E_{ext}$ may be considered as a process of attracting the triangle to an image feature, such as a boundary.

The affine transformations $T_k[m_i]$ and weights $\omega_{i,k}$ define the variability of the mean shape $m_i$. Deviation of the vector $(v_i-v_j)$ between a model point with index i and a neighbouring model point with index j∈N (i) with respect to the corresponding vector of the transformed mean shape will cause $E_{int}$ to increase. In this way, the $E_{int}$ term serves to constrain the model such that it does not depart too far from the mean shape. This assists in particular with segmenting regions with weak boundaries.

In order to effect such a model-based segmentation, the heart must first be localized in the image. Localization may be achieved via a completely automatic method, e.g. using a generalized Hough Transform (GHT). In such a technique, the center of gravity of the initial triangle mesh model is placed into a 3D image according to an optimal position obtained by a GHT. The initial mesh model is thus translated and scaled so as to be positioned in the image, as is well-known per se.

Alternatively or additionally, other localization techniques such as 'Hough forests' and classification approaches may be used.

Following localization, the segmentation routine may then be implemented in order to adapt the model to the organ boundaries. The segmentation routine may be a model-based segmentation routine which may be carried out in multiple steps, leading from a very coarse to a finer adaption. In such a routine, the initial mesh may be adapted rigidly by scaling, shifting and rotating the whole mesh using a global similarity transformation. This may be followed by a global affine transformation to allow for squeezing or stretching of the heart and a multi affine transformation which adapts anatomical regions such as ventricles and atria individually. The mesh resulting from previous adaptations may then be adapted in a deformable fashion, i.e. each triangle of the mesh is allowed to move independently.

It is noted that in the first segmentation, the poorer image quality of the non-contrast agent-enhanced ultrasound image, e.g. relative to the contrast agent-enhanced ultrasound image, may lead to a sub-optimal segmentation. However, the first segmentation may nevertheless result in a first anatomical model which is closer to the actual organ shape of the patient than the mean shape of the initial anatomical model, i.e. the initial mesh.

In an embodiment, the performing 250 a second segmentation may comprise using the first anatomical model to initialize the second segmentation. In such an embodiment, the first anatomical model may be used instead of the mean shape, i.e. of the initial mesh model. This may enhance the efficiency and quality of the second segmentation because the first anatomical model will be closer to the actual organ shape of the patient compared to the mean shape.

Alternatively, the mean shape may be used to initialize the second segmentation. It is further noted that the order of steps 230 and 250 depicted in FIG. 2 may, for instance, be reversed. It is thus conceivable to initialize the first segmentation 230 using the second anatomical model resulting from the second segmentation 250 of the contrast agent-enhanced ultrasound image.

Following steps 230 and 250, the first and second anatomical models may be aligned, i.e. registered. Registration of the first and second anatomical models may be performed in any suitable manner. When model-based segmentation has been employed in steps 230 and 250, the resulting respective triangular meshes (having identical or very similar topology) may be registered using the vertex coordinates of the respective mesh models. In other words, the first and second anatomical models may be used to calculate a transformation in order to register the non-contrast agent-enhanced and contrast agent-enhanced ultrasound images. To this end, a rigid registration matrix may be calculated from the respective meshes, i.e. their vertices, and applied to the images. Use of the first and second anatomical models, e.g. mesh models, for registration of the contrast agent-enhanced and non-contrast agent-enhanced ultrasound images may facilitate and improve the alignment of the respective images in step 260.

In step 270, a combined segmentation of the aligned non-contrast agent-enhanced and contrast agent-enhanced ultrasound images generates the combined anatomical model. The combined segmentation 270 may be achieved, for instance, by using the model-based segmentation technique briefly described above in relation to the first segmentation 230 and the second segmentation 250. However, using the aligned non-contrast agent-enhanced and contrast agent-enhanced images for the combined segmentation 270 means that a more accurate and robust segmentation can be obtained compared to that which can be obtained from, for instance, segmenting either the contrast agent-enhanced ultrasound image or the non-contrast agent-enhanced ultrasound image alone. The use of the non-contrast agent-enhanced ultrasound image means that it is possible for the combined segmentation to take account of other cardiac structures, e.g. the mitral valve, in addition to the left ventricle; these other cardiac structures not being visible in the contrast agent-enhanced ultrasound image. In this way, the generation of the combined anatomical model in step 270 exploits the respective advantages of the non-contrast agent-enhanced and contrast agent-enhanced ultrasound imaging techniques.

The present method 200 is thus distinguished with respect to conventional approaches involving segmentation of the contrast agent-enhanced ultrasound image alone which may be based on an (erroneous) assumption that all of the requisite information is present in the contrast agent-enhanced ultrasound image. In other words, conventional approaches may neglect the non-contrast agent-enhanced ultrasound image for the purposes of segmentation. The present method 200 includes the information from the non-contrast agent-enhanced ultrasound image in the combined segmentation 270.

The performing 270 a combined segmentation comprises using features of both of the aligned non-contrast agent-enhanced and contrast agent-enhanced ultrasound images as target points. The target point $x_i^{target}$ has been discussed above in relation to the model-based segmentation technique. Owing to the differences in the nature and quality of the information available from the respective contrast agent-enhanced and non-contrast agent-enhanced ultrasound images, respective target points corresponding to the contrast agent-enhanced and non-contrast agent-enhanced components of the aligned image may not match. In such a scenario, the discrepancy between the respective target points may be resolved by, for instance, taking a simple mean of the respective points.

More preferably, the respective target points of the contrast agent-enhanced and non-contrast agent-enhanced ultrasound images may be weighted relative to each other such that a weighted target point for a given triangle may be employed for the combined segmentation which is the same for both of the respective images but which prioritizes the image giving the stronger feature response. Such a weighting may be based on the particular region given that some regions are more clearly visible in the contrast-agent-enhanced ultrasound image and others are more clearly visible in the non-contrast-agent-enhanced ultrasound image, as previously described. For example, the weighting used for a left ventricle myocardial boundary may favour the contrast agent-enhanced component of the aligned images.

In an embodiment, the aligning 260 of the non-contrast agent-enhanced and contrast agent-enhanced ultrasound images and the performing 270 the combined segmentation may be repeated in a plurality of cycles. This is depicted in FIG. 2 by the boxes corresponding to steps 260 and 270 being connected by arrows so as to form a loop. This is further depicted in FIG. 3 by the double arrows between steps 260 and 270 (encompassed by the hashed oval).

The quality of the combined segmentation 270 may partly depend on the quality, i.e. closeness, of the alignment of the images in step 260. Equally, the alignment of the images may be enhanced by a better segmentation, particularly when the alignment is performed via prior segmentation, i.e. in steps 230 and 250. Hence repeating, e.g. iterating, this procedure may improve the combined segmentation result. The number of cycles may be a set or pre-programmed number, e.g. 2-5 cycles. Alternatively, the number of cycles may, for instance, be based on convergence of one or more model-based segmentation parameters. The method 200 shown in FIG. 2 terminates in step 280.

Whilst not shown in FIG. 2, the method may further comprise a visualization step 290, as shown in FIG. 3. The visualization 290 of the combined anatomical model will now be described in relation to the ultrasound system.

It is noted at this point that visualization of the combined anatomical model may not be required. For example, determination of left ventricular quantities, e.g. volume, may be attained from the combined anatomical model without any requirement to view the combined segmented image. Accordingly, the conversion module and the display device may be not be included in a simplified ultrasound system which is, for instance, only configured to provide quantification without visualization of the combined anatomical model.

The ultrasound system comprises an ultrasonic transducer array 100 capable of emitting and receiving ultrasonic signals, and a signal processor 22 adapted to compile the received ultrasonic signals into a non-contrast agent-enhanced ultrasound image when no contrast agent is used, and a contrast agent-enhanced ultrasound image when a contrast agent is used. The ultrasound system includes the processor arrangement which is adapted to implement the method 200, as described above. A conversion module converts the combined anatomical model generated by the processor arrangement to a combined segmented image. A display device 40 displays the combined segmented ultrasound image and a user interface 38 permits a user to control the processor arrangement to generate the combined anatomical model.

The processor arrangement may implement the various steps of the method 200 without the requirement for user intervention. This may assist to ensure that reproducible results are obtained. The user interface 38 may control, i.e. trigger, the processor arrangement to implement the method 200 so as to generate the combined anatomical model. The user interface 38 may comprise a button or switch which may be pressed to trigger the method 200, for instance, prior to acquisition of the contrast agent-enhanced image, i.e. prior to injection of the contrast agent. This button may also, for example, simultaneously switch the acquisition parameters to the desired mode for obtaining a contrast agent-enhanced image.

In an embodiment, the user interface 38 may be adapted to permit user selection of the viewing plane of the displayed combined segmented ultrasound image. Any suitable user interface may employed such as a touchscreen, keyboard etc. Owing to the alignment of the contrast agent-enhanced and non-contrast agent-enhanced ultrasound images for generation of the combined segmented image, the respective images are thus anatomically synchronized. Accordingly, when the viewing plane is adjusted for the non-contrast agent-enhanced image, the contrast agent-enhanced image will be also adjusted to the same viewing plane, and vice versa. This is of clear benefit in terms of facilitating visual comparison of the respective images.

The processor arrangement may be adapted to implement a post-visualization routine comprising a further aligning of the non-contrast agent-enhanced and contrast agent-enhanced ultrasound images and a further performing of the combined segmentation. The user interface 38 may permit the user to trigger this post-visualization routine following inspection of the combined segmented image. In this way, the user may opt to seek improvement of the combined anatomical model by triggering the processor arrangement to implement the further alignment and further combined segmentation steps.

In an embodiment, the processor arrangement may be adapted to invert the contrast agent-enhanced ultrasound image, to normalize the inverted contrast agent-enhanced ultrasound image based on the non-contrast agent-enhanced ultrasound image, and to control the display device 40 to display the inverted and normalized contrast agent-enhanced ultrasound image. As is well-known per se, the contrast agent-enhanced image, e.g. the LVO image, may show the left ventricle as a brighter region in comparison to, for instance, the myocardium. On the other hand, in the non-contrast agent-enhanced image, e.g. the TTE image, the myocardium may show up brighter than the left ventricle but the contrast between the two regions may be lower than in the contrast agent-enhanced image. Thus inverting the contrast agent-enhanced ultrasound image and normalizing it based on the non-contrast agent-enhanced ultrasound image may facilitate comparison of the respective images. It is noted that image inversion and normalization techniques are well-known per se and will not be described herein for the sake of brevity only.

The processor arrangement may be adapted to overlay the non-contrast agent-enhanced and contrast agent-enhanced ultrasound images, and to control the display device to display the overlay. The combined segmented image may be also overlaid on the respective ultrasound images. The user interface 38 may be adapted to permit user adjustment of the relative contributions of the non-contrast agent-enhanced and contrast agent-enhanced ultrasound images in the overlay. In a non-limiting example, false color rendering may be used to assist the user to differentiate between the respective images. The user interface 38 may comprise a dial or slider such that the user is able to make this adjustment by sliding the slider or rotating the dial. The direction of sliding or rotating may determine which of the respective images contributes more in the overlay. In this way, the user may easily assess how closely the combined segmented image fits each of the respective contrast agent-enhanced and non-contrast agent-enhanced ultrasound images.

Alternatively or additionally, the processor arrangement may be adapted to control the display device 40 such that the combined segmented ultrasound image is displayed in separate image panes which respectively comprise the non-contrast agent-enhanced and contrast agent-enhanced ultrasound images.

In an embodiment, the processor arrangement may be adapted to modify the combined segmented image displayed in both image panes in response to user instructions to modify the combined anatomical model.

The processor arrangement may further be configured to permit manual editing of the combined anatomical model. Such editing may, for instance, involve manual modification to the weighting used for one or more of the weighted target points described above in respect of the combined segmentation 270. In such an example, the user may deem that the weighting used by the processor arrangement during (automatic) implementation of the method 200 is too heavily in favour of one of the respective contrast agent-enhanced and non-contrast agent-enhanced ultrasound images, and may adjust the weighting accordingly. The user interface 38 may comprise controls for inputting the user instruction.

Changes to the combined anatomical model and thus the combined segmented image which may be applied in respect of one image pane are applied in both image panes. In this way, the user may assess the modification to the combined segmented image with reference to both the contrast agent-enhanced and non-contrast agent-enhanced images.

As discussed above, embodiments make use of a processor arrangement for performing the data processing steps. The processor arrangement can be implemented in numerous ways, with software and/or hardware, to perform the various functions required. A processor is one example of a controller which employs one or more microprocessors that may be programmed using software (e.g., microcode) to perform the required functions. A controller may however be implemented with or without employing a processor, and also may be implemented as a combination of dedicated hardware to perform some functions and a processor (e.g., one or more programmed microprocessors and associated circuitry) to perform other functions.

Examples of controller components that may be employed in various embodiments of the present disclosure include, but are not limited to, conventional microprocessors, application specific integrated circuits (ASICs), and field-programmable gate arrays (FPGAs).

In various implementations, a processor or controller may be associated with one or more storage media such as volatile and non-volatile computer memory such as RAM, PROM, EPROM, and EEPROM. The storage media may be encoded with one or more programs that, when executed on one or more processors and/or controllers, perform at the required functions. Various storage media may be fixed within a processor or controller or may be transportable, such that the one or more programs stored thereon can be loaded into a processor or controller.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

The invention claimed is:

1. A method for generating a combined anatomical model of a heart, the method comprising:

receiving a non-contrast agent-enhanced ultrasound image of a left ventricular region of the heart;
receiving a contrast agent-enhanced ultrasound image of the left ventricular region of the heart;
aligning the non-contrast agent-enhanced and contrast agent-enhanced ultrasound images; and
performing a combined segmentation of the aligned non-contrast agent-enhanced and contrast agent-enhanced ultrasound images to generate the combined anatomical model, wherein the combined anatomical model comprises a mesh model, wherein the mesh model comprises a plurality of shapes associated with target points, wherein performing the combined segmentation comprises using features of both of the aligned non-contrast agent-enhanced and contrast agent-enhanced ultrasound images as the target points.

2. The method of claim 1,
further comprising:
performing a first segmentation of said non-contrast agent-enhanced ultrasound image to generate a first anatomical model; and
performing a second segmentation of said contrast agent-enhanced ultrasound image to generate a second anatomical model,
wherein the aligning the non-contrast agent-enhanced and contrast agent-enhanced ultrasound images comprises registration of said first and second anatomical models.

3. The method of claim 2, wherein the performing a second segmentation comprises using said first anatomical model to initialize said second segmentation.

4. The method of claim 1, wherein the receiving a contrast agent-enhanced ultrasound image comprises combining a plurality of ultrasound image frames obtained during respective heart cycles in which a contrast agent is present.

5. The method of claim 1,
wherein the combined segmentation is a model-based segmentation, and
wherein performing a combined segmentation comprises adapting a generic anatomical model to the aligned non-contrast agent-enhanced and contrast agent-enhanced ultrasound images using the target points.

6. The method of claim 1, wherein the aligning of the non-contrast agent-enhanced and contrast agent-enhanced ultrasound images and the performing the combined segmentation are repeated in a plurality of cycles.

7. A non-transitory computer-readable medium comprising a computer program which is adapted, when said computer program is run on a computer, to implement the method of claim 1.

8. A processor arrangement for controlling generation of a combined anatomical model of a heart, wherein the processor arrangement is adapted to:
receive a non-contrast agent-enhanced ultrasound image of a left ventricular region of the heart;
receive a contrast agent-enhanced ultrasound image of the left ventricular region of the heart;
align the non-contrast agent-enhanced and contrast agent-enhanced ultrasound images; and
perform a combined segmentation of the aligned non-contrast agent-enhanced and contrast agent-enhanced ultrasound images to generate the combined anatomical model, wherein the combined anatomical model comprises a mesh model, wherein the mesh model comprises a plurality of shapes associated with target points, wherein performing the combined segmentation comprises using features of both of the aligned non-contrast agent-enhanced and contrast agent-enhanced ultrasound images as the target points.

9. An ultrasound system comprising:
an ultrasonic transducer array, wherein the ultrasonic transducer array is capable of emitting and receiving ultrasonic signals;
a signal processor adapted to compile the received ultrasonic signals into the non-contrast agent-enhanced ultrasound image when no contrast agent is used and the contrast agent-enhanced ultrasound image when a contrast agent is used;
the processor arrangement as claimed in claim 8, wherein the processor arrangement is adapted to convert the combined anatomical model to a combined segmented image;
a display device for displaying the combined segmented ultrasound image; and
a user interface adapted to permit a user to control the processor arrangement to generate said combined anatomical model.

10. The ultrasound system of claim 9,
wherein the processor arrangement is adapted to implement a post-visualization routine comprising:
a further aligning of the non-contrast agent-enhanced and contrast agent-enhanced ultrasound images; and
a further performing of the combined segmentation,
wherein the user interface is adapted to permit a user to trigger said post-visualization routine.

11. The ultrasound system of claim 9, wherein the processor arrangement is adapted to:
invert the contrast agent-enhanced ultrasound image;
normalize the inverted contrast agent-enhanced ultrasound image based on the non-contrast agent-enhanced ultrasound image; and
control the display device to display said inverted and normalized contrast agent-enhanced ultrasound image.

12. The ultrasound system of claim 9, wherein the processor arrangement is adapted to:
overlay the non-contrast agent-enhanced ultrasound image, the contrast agent-enhanced ultrasound image and the combined segmented image; and
control the display device to display the overlay.

13. The ultrasound system of claim 12, wherein the user interface is adapted to permit user adjustment of the relative contributions of the non-contrast agent-enhanced and contrast agent-enhanced ultrasound images in the overlay.

14. The ultrasound system of claim 9, wherein the processor arrangement is adapted to control the display device such that said combined segmented ultrasound image is displayed in separate image panes which respectively comprise the non-contrast agent-enhanced and contrast agent-enhanced ultrasound images.

15. The ultrasound system of claim 14,
wherein the processor arrangement is adapted to modify the combined segmented image displayed in both image panes in response to user instructions to modify the combined anatomical model,
wherein the user interface comprises controls for inputting said user instruction.

16. The ultrasound system of claim 9, wherein the processor arrangement is adapted to weigh respective target points of the aligned non-contrast agent-enhanced and contrast agent-enhanced ultrasound images relative to each other for performing the combined segmentation.

17. The ultrasound system of claim 16, wherein the processor arrangement is further adapted to permit manual modification to the weighting used for one or more of the weighted target points.

18. The method of claim 1, wherein performing the combined segmentation further comprises weighting respective target points of the aligned non-contrast agent-enhanced and contrast agent-enhanced ultrasound images relative to each other.

19. The method of claim 18, wherein the weighting for a given target point of the respective images prioritizes the image giving the stronger feature response.

20. The method of claim 19, wherein the weighting for said target point is based on the particular region of the heart in which said target point is located.

* * * * *